United States Patent

Coles et al.

(12)
(10) Patent No.: US 6,900,441 B2
(45) Date of Patent: May 31, 2005

(54) MULTIPLE SIMULTANEOUS ACQUISITION OF GAMMA CAMERA DATA SETS

(75) Inventors: David E. Coles, San Francisco, CA (US); Douglas Murray, Castro Valley, CA (US); Hugo Bertelsen, Aalborg (DK)

(73) Assignee: Koninklijke Philips Electronics N.V., Eindhoven (NL)

( * ) Notice: Subject to any disclaimer, the term of this patent is extended or adjusted under 35 U.S.C. 154(b) by 628 days.

(21) Appl. No.: 09/894,277

(22) Filed: Jun. 27, 2001

(65) Prior Publication Data

US 2003/0001099 A1 Jan. 2, 2003

(51) Int. Cl.⁷ .................................................. G01T 7/00
(52) U.S. Cl. ...................................... 250/369; 250/368
(58) Field of Search ........................... 250/369, 363.03, 250/363.04, 363.09; 700/17

(56) References Cited

U.S. PATENT DOCUMENTS

| | | | |
|---|---|---|---|
| H12 H | | 1/1986 | Bennett et al. |
| 4,641,328 A | | 2/1987 | Fujise |
| 5,431,161 A | | 7/1995 | Ryals et al. |
| 5,803,914 A | * | 9/1998 | Ryals et al. ............... 600/407 |
| 6,255,655 B1 | * | 7/2001 | Mc Croskey et al. ... 250/363.03 |
| 6,337,481 B1 | * | 1/2002 | Stearns et al. ......... 250/363.03 |
| 2003/0004584 A1 | * | 1/2003 | Hallett ....................... 700/17 |

\* cited by examiner

*Primary Examiner*—Otilia Gabor
(74) *Attorney, Agent, or Firm*—Eugene E. Clair, Esq.

(57) ABSTRACT

A gamma camera system is described in which multiple simultaneous acquisitions are performed based upon different characteristics for event data acquired by a common gantry behavior. The event data from a detector is selected for different images based upon characteristics such as gating, ungated, energy windows, or zooming.

16 Claims, 5 Drawing Sheets

FIG. 3

Gated Parameters

No. of Gated Frames ___331___

% R-R Interval Variance

Max % Window ___333___

Min % Window ___335___

R-R Interval Fixed ___337___

R-R Interval Vary ___339___

No. Exclude After Variance ___341___

Time Per ECT Azimuth or Total Beats ___343___

Procedure ID: Gated Spect ⸺ 300

Spect Parameters

Degrees in Orbit: ___301___
Images in Orbit: ___303___
Matrix Size: ___305___
Starting Location: ___307___
Rotation Direction: ___309___
Orientation: ___311___
Orbit (circular): ___313___
Flood Correction: ___315___
Acquisition Method: ___317___

Isotope ID: ___351___
Patient ID: ___353___
View ID: ___355___

Processing ___357___

Time _____ Avg R-R _____
Frame No. _____ Gated Frames _____
Max Frame _____ Max Frames _____
Counts/Sec _____
Beats _____

___365___

MULTIPLE SIMULTANEOUS ACQUISITION OF GAMMA CAMERA DATA SETS

This invention relates to nuclear (gamma camera) imaging systems and, in particular, to gamma cameras which acquire multiple data sets simultaneously during a study.

When diagnosing a patient in a gamma camera study, the results of one study at times can determine whether another different study is required. For example, a cardiac study may acquire gated event data for imaging a particular phase of the heart cycle such as end-diastole. However, if the heartbeat is irregular, the acquired data set can be non-diagnostic, as it can be contaminated with event data acquired at times other than the desired phase of the heart cycle. In such a case the clinician may then decide to do an ungated study, where the irregular heartbeat is less of an obstacle to the intended data acquisition. This of course mandates a second study and may require a second dosing of the patient with the radionuclide. It would be desirable to be able to obviate the need for such subsequent studies so as to make more efficient use of the patient's time and the utilization of the gamma camera, and to obviate the need for repeated exposure of the patient to radionuclides.

In accordance with the principles of the present invention, a gamma camera system acquires multiple data sets during a single protocol. The data sets are used to produce different types of images from the same protocol. If one type of image proves to be diagnostically unsuitable or ambiguous at the conclusion of the protocol, one of the alternate types of images may provide images which are more desirable for the diagnosis. Since the multiple acquisitions are done during performance of the same protocol, the different studies must be compatible with the same camera gantry behavior. The gamma camera system automatically checks for and prevents attempts to perform incompatible studies simultaneously. The inventive system can prevent the need for repeated studies by providing different data sets from the same protocol.

In the drawings:

FIG. 3 illustrates some of the parameters which may be used in a gated SPECT study;

Figure 1:
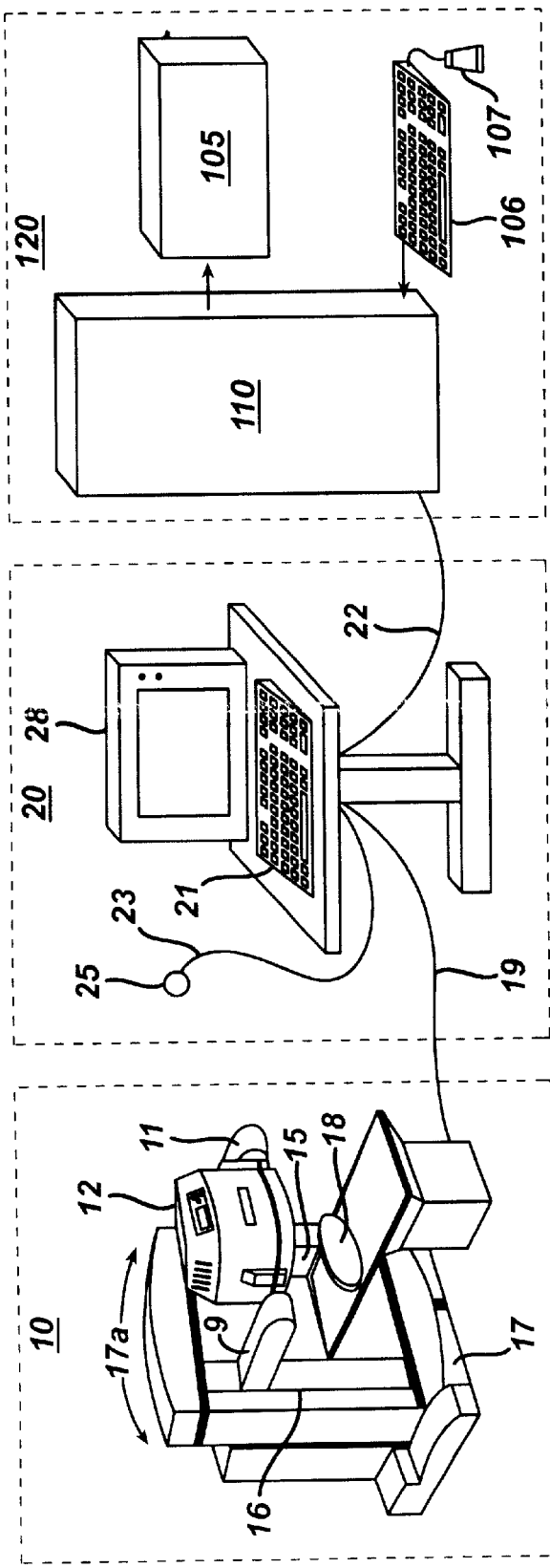
FIG. 1 illustrates the major components of a gamma camera system.

FIG. 1 illustrates the major components of a nuclear camera image acquisition, processing and display system. The present invention includes either a single head (single detector) camera 10 as shown in the drawing or a dual head (dual detector) camera as shown in U.S. Pat. No. 5,760,402 (Hug. et al.) or U.S. Pat. No. 6,150,662 (Hug et al.). These camera systems are SPECT cameras ideal for cardiac, abdominal, and whole body studies and are capable of implementing gated SPECT imaging techniques. In the illustration of FIG. 1, two arms 11 and 9 mounted on vertical tracks 16 and 15 form a gantry structure that can move the detector head 12 in various projection angles to accomplish the required 180 and 360 degree movements of the detector 12 used in gated SPECT studies. Pivot structure 17 allows the camera detector 12 and gantry structure to pivot clockwise or counterclockwise. The camera system 10 includes a detector head 12 comprising a number of well known radiation detection components of the Anger camera type including a photomultiplier array, a collimator, a scintillating crystal and a digital pixel output. The camera system 10, in a well known fashion, images the patient to provide digital image data which is binned according to particular discrete angles of rotation in which the detector 12 traverses about the patient. Binning can also occur according to particular phases of the cardiac cycle (R–R interval, defined below). For each angle of rotation, several phases of the cardiac cycle may be interrogated. Particular (x,y) coordinate positions within the imaging detector of the camera system are called pixel locations and the number of scintillations detected by each pixel location is represented by a count value for that pixel. Each pixel contains a count value representing the number of radiation emissions detected at that location of the detector 12. The resulting digital image data from the camera system 10 is binned according to the particular discrete angle of rotation in which the detector was situated when the image data was acquired. Also binned is the gated segment (phase) within the R–R interval in which the data was acquired in gated SPECT studies. The pixel matrix of (x,y) locations is referred to herein as a histogram of scintillations at these coordinate locations. It is understood that a histogram represents a raw image. For example, a typical detector 12 may have a resolution of (64×64) pixels or (128×128) pixels available for imaging and is capable of imaging at a maximum resolution of approximately (1000×1000) pixels.

The camera system 10 is coupled to a data acquisition computer system 20, which in a particular constructed embodiment is implemented using a general purpose computer system having high speed communications ports for input and output coupled to a two-way data transmission line 19 coupling the camera system 10 to the computer system 20. The computer system 20 communicates data acquisition parameters (also called data acquisition protocols) selected by a user to the camera system 10 to initiate a particular type of study by the camera system 10. The imaging data from the camera system 10 is then transferred over line 19 to the communications device of the system 20 and this raw gated SPECT image data is then forwarded to a post acquisition processing computer system 120. The data acquisition system 20 also comprises a keyboard entry device 21 for user interface to allow selection and modification of predefined data acquisition parameters which control the imaging processes of the camera system 10. Also coupled to the data acquisition system 20 is a standard color display monitor 28 for display of parameter information and relevant information regarding the particular gated SPECT study underway such as imaging status communicated from the camera system 10 during an imaging session.

For a gated SPECT study a cardiac electrode and signal amplification unit 25 is also coupled to the data acquisition computer system 20. This unit 25 is specially adapted to couple with a patient's chest near the heart to receive the heartbeat electrical signal. The unit 25 is composed of well known heartbeat detection and amplification (EKG) components and any of several well known devices can be utilized within the scope of the present invention. In order to perform gated SPECT analysis on the heart, the heartbeat pulse or electrical wave must be studied for each patient, as each heart is different. The heartbeat wave is examined to determine the points within the cycle where the well-known R wave is encountered. The time interval between successive R waves is measured to determine the R–R interval. These points and timing intervals between these points will be used to gate the imaging process of the camera system 10 during the cardiac cycle and particularly at the end-diastole and end-systole interval segments. The preferred embodiment of the present invention automatically, under control of the system 20, collects five sample heartbeat waves once the detector 25 is located on the subject patient in order to determine the average R–R period. This information is fed to the computer system 20 and then sent to the camera system 10. However such information could also be detected and determined directly by the computer system 10 once conditioned to do so by the acquisition computer system 20 under user control. For a particular projection angle, the system 10 directs the acquired imaging counts to the first segment bin, and upon each successive time interval the image data is directed to a new gated bin. When the R wave is detected once more, the first bin receives the image data again and the process continues through each other segment and associated bin until a new projection angle is encountered. The electrode 25 also is used by the camera system 10 in order to detect the start of a cardiac cycle and gate the camera imaging system appropriately depending on the number of selected segments of the R–R interval used for collection.

As discussed above, the data acquisition portion of the imaging system is composed of camera system 10 and computer system 20. Referring still to FIG. 1, the image data is sent from the camera system 10 over line 19 to acquisition system 20 and then over line 22 to the post acquisition processing system 120. This system 120 is responsible for processing, displaying and quantifying certain data acquired by system 10 and system 20. Specifically, the system 120 can process and uniquely display quantitative information regarding blood flow within the myocardium (perfusion) and wall motion of the myocardium (function) as a result of the gated SPECT data acquired.

The post acquisition processing system 120 acquires the raw gated SPECT image data generated by the camera system 10 and, using user configurable procedures, reconstructs (performs tomography or backprojection) the data to provide a reconstructed volume and from the volume generates specialized planar or volumetric images for diagnosis, including generating and displaying the functional images as described above. In cardiac imaging the generated images or frames represent different slices of the reconstructed heart volume at variable thicknesses in a short axis dimension, a vertical dimension and a horizontal dimension (all three are user configurable) for a number of gated time segments. Therefore, complete three dimensional information can be displayed by display 105 in a two dimensional manner in a variety of formats and orientations including a display providing quantitative information regarding both wall thickening (perfusion) and wall motion (function) of the myocardium under study.

Figure 2:
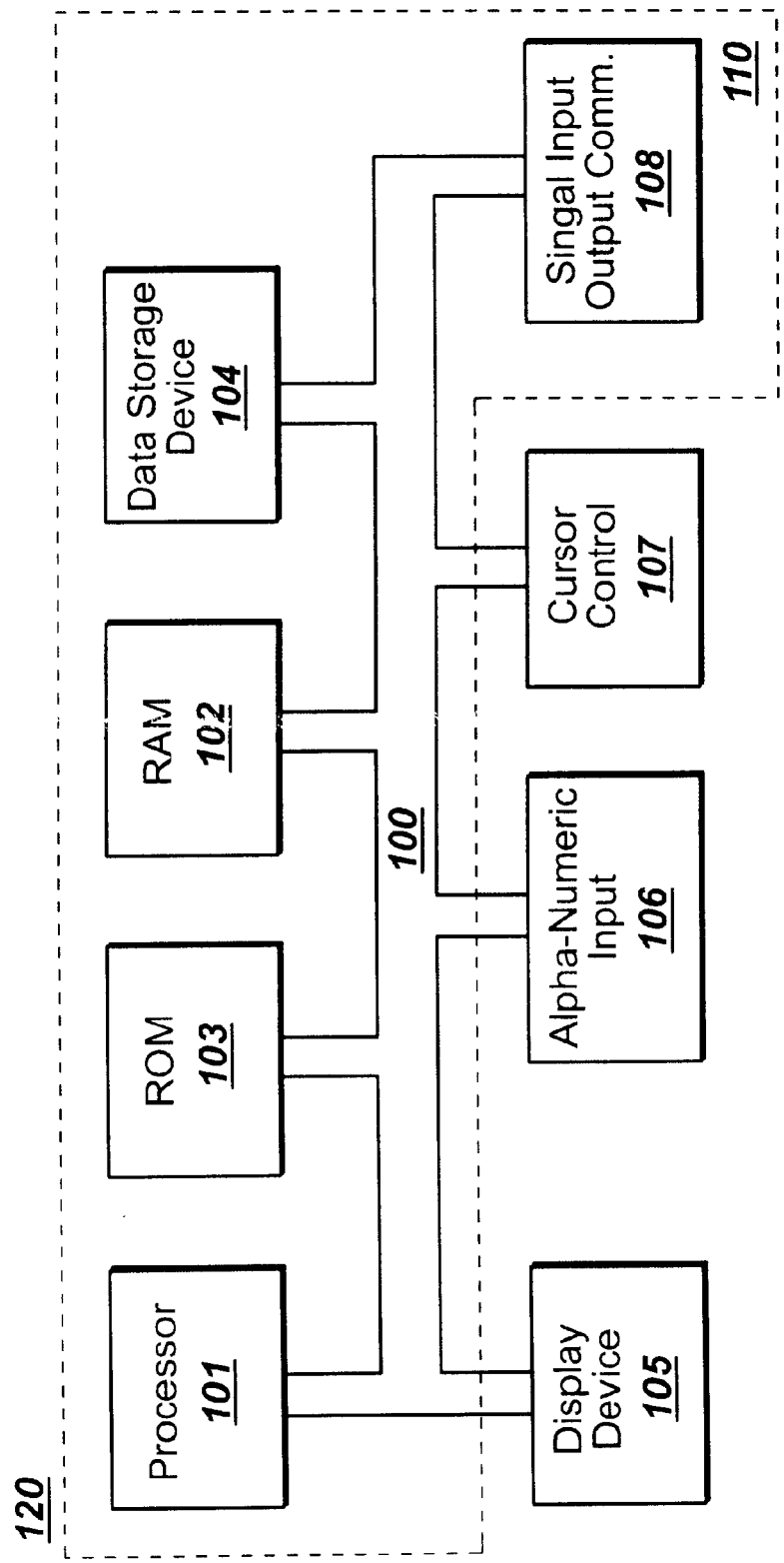
FIG. 2 illustrates in block diagram form the post data acquisition processing and display system of the gamma camera of FIG. 1.

The computer of the post acquisition processing system 120 in a constructed embodiment illustrated in FIG. 2 is a SPARC system available from Sun Microsystems of California, however any number of similar computer systems having the requisite processing power and display capabilities will suffice within the scope of the present invention. Generally, the system 120 comprises a bus 100 for communicating information, a central processor 101 coupled with the bus for processing information (such as image data and acquired counts) and command instructions, a random access memory 102 coupled with the bus 100 for storing information and instructions for the central processor 101, a read only memory 103 coupled with the bus 100 for storing static information and command instructions for the processor 101, a data storage device 104 such as a magnetic disk or optical disk drive coupled with the bus 100 for storing information (such as both raw gated SPECT and reconstructed data sets) and command instructions, and a display device 105 coupled to the bus 100 for displaying information to the computer user. There is also an alphanumeric input device 106 including alphanumeric and function keys coupled to the bus 100 for communicating information and command selections to the central processor 101, a cursor control device 107 coupled to the bus for communicating user input information and command selections to the central processor 101 based on hand movement, and an input and output device 108 coupled to the bus 100 for communicating information to and from the computer system 120. The input and output device 108 includes, as an input device, a high speed communication port configured to receive image data acquired by the nuclear camera system 10 and fed over line 22.

The display device 105 utilized with the system of the present invention may be a liquid crystal device, cathode ray tube, or other display device suitable for creating graphic images and alphanumeric characters recognizable to the user. The display unit 105 of the preferred embodiment of the present invention is a high resolution color monitor. The cursor control device 107 allows the computer user to dynamically signal the two dimensional movement of a visible symbol or cursor 5 (pointer) on a display screen of the display device 105. Many implementations of the cursor control device are known in the art including a trackball, mouse, joystick or special keys on the alphanumeric input device 105 capable of signaling movement of a given direction or manner of displacement. It will be appreciated that the cursor control device 107 also may be directed and/or activated via input from the keyboard using special keys and key sequence commands, or from a touchscreen display device. In the discussions regarding cursor movement and/or activation within the preferred embodiment, it is to be assumed that the input cursor directing device may consist of any of those described above and is not limited to the mouse cursor device. It will be appreciated that the computer chassis 110 may include the following components of the image processor system: the processor 101, ROM 103, RAM 102, the data storage device 104, and the signal input and output communication device 108 and optionally a hard copy printing device.

The data acquisition system 20 allows a user via keyboard control to select and/or create a predefined set of parameters (or protocols) for direction of a gated SPECT imaging session or other selected study by the camera system 10. FIG. 3 illustrates a parameter interface screen and configurable parameters of a nuclear camera system for data acquisition that are selected and displayed on a screen by the user via keyboard 21. FIG. 3 illustrates some of the parameters that are configurable by the data acquisition system 20. It is appreciated that once set, the configurable parameters can be saved and referenced in a computer file for subsequent recall. The stored parameters or protocol file can then be recalled and utilized for a particular study, thus eliminating the need to again enter the parameters for similar or identical studies. The name of the parameter file shown in FIG. 3 is "GATED SPECT" and is indicated at 300. It is appreciated that the computer system 20, once instructed by the user, will relay the parameters set by the user to the camera system 10 in order to initialize and begin a particular study. The initiation is done by selection of processing command 357. A user interface of this type is thus versatile while at the same time providing a high degree of automation of the execution of selected study protocols.

Figure 4:
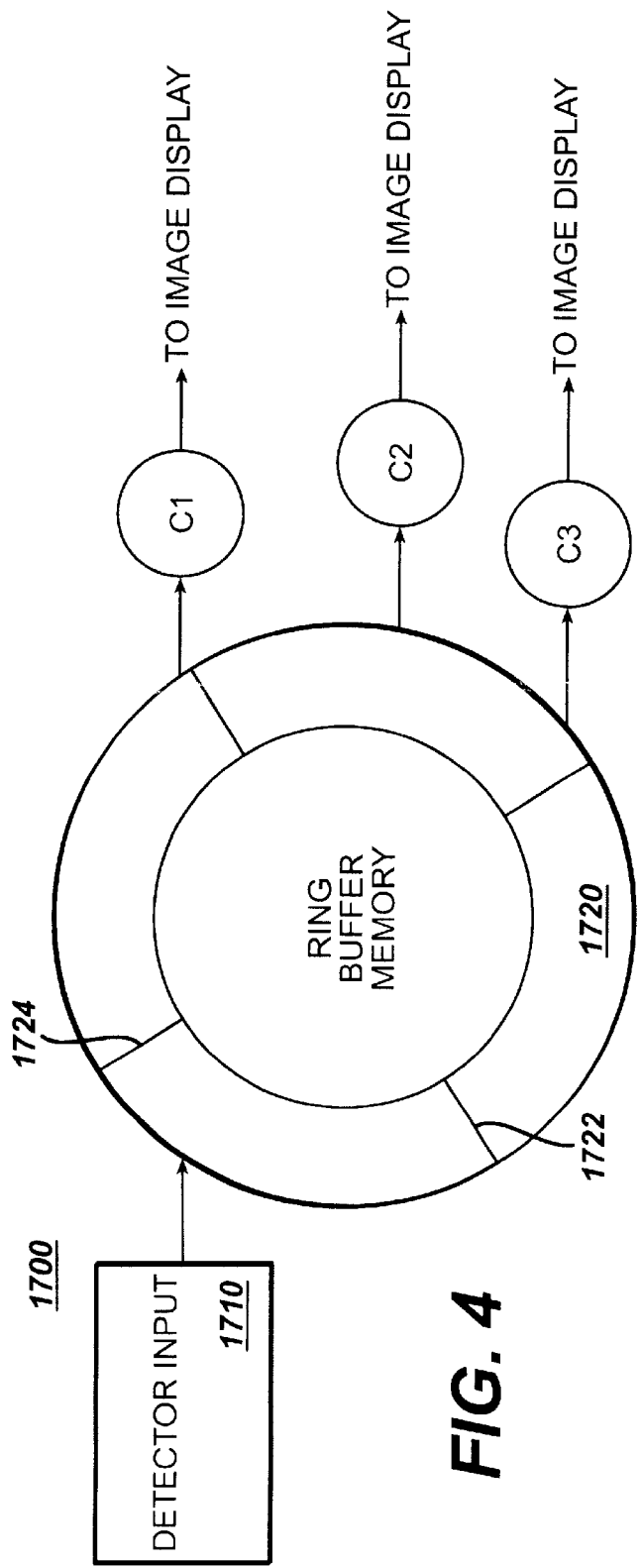
FIG. 4 illustrates in block diagram form a network of the gamma camera which simultaneously processes different data sets from the same imaging procedure in accordance with the principles of the present invention.

In accordance with the principles of the present invention, the gamma camera system of FIGS. 1–3 is capable of performing several studies simultaneously by use of the data network shown in FIG. 4. The network includes a ring buffer 1720 into which gamma camera data is entered at a high data rate. The data in the illustrated ring buffer 1720 may have a specified start point 1722 and an end point 1724 that may adjust around the ring buffer as data is received and processed. The gamma camera data is entered into the ring buffer by one or more Producers, one of which is shown at 1700. A Producer is a camera subsystem or data path which enters data into the ring buffer 1720. The Producer illustrated in the drawing is a data stream 1710 from a detector or camera head, which inputs detector data into the ring buffer. Other Producers may provide data from other sources such as stored data sources, for example. Some of the types of data words which are provided by a detector are described in FIG. 6 below.

Accessing the data which traverses the ring buffer 1720 are one or more Consumers. Three Consumers are shown in FIG. 4, and are labeled C1, C2, and C3. A Consumer is a data processor or path or other entity which makes use of some or all of the data in the ring buffer 1720. In the illustrated embodiment each Consumer is an entity conditioned to look for specific characteristics of event data and to read data from the ring buffer selected for a particular type of study. The studies in the following examples are all associated with types of images and hence the Consumers shown in this example read and process selected data into images, which can then be forwarded to an image display. Each Consumer C1, C2 and C3 examines the data in the ring buffer as it passes by its input, and independently reads those data words which are needed for the studies being supported by that Consumer. The Consumers operate both independently and simultaneously, and each can support one or more imaging processes.

Figure 5:
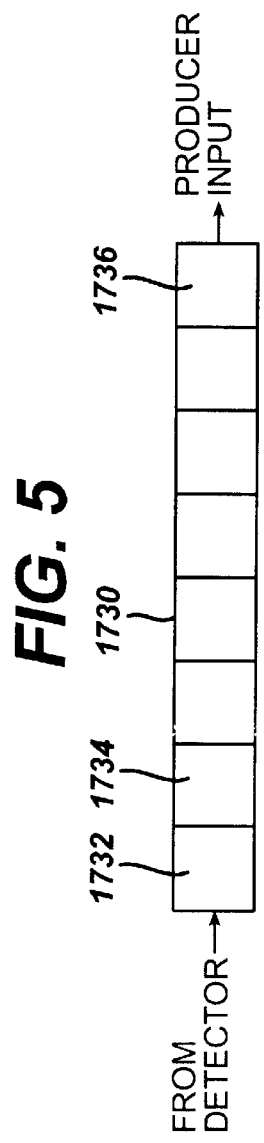
FIG. 5 illustrates a high speed data path from which the Producer of FIG. 4 reads input data.

In a constructed embodiment the data from a detector, being produced in real time as the detector head detects scintillation events, is provided over a high speed data path 1730 as illustrated in FIG. 5. The stream of data words is provided serially from the detector as indicated by sequential data locations 1732, 1734 . . . 1736. The data at the output of the data path 1730 is read by the input of a Producer, which enters the data into the ring buffer 1720.

Figure 6:
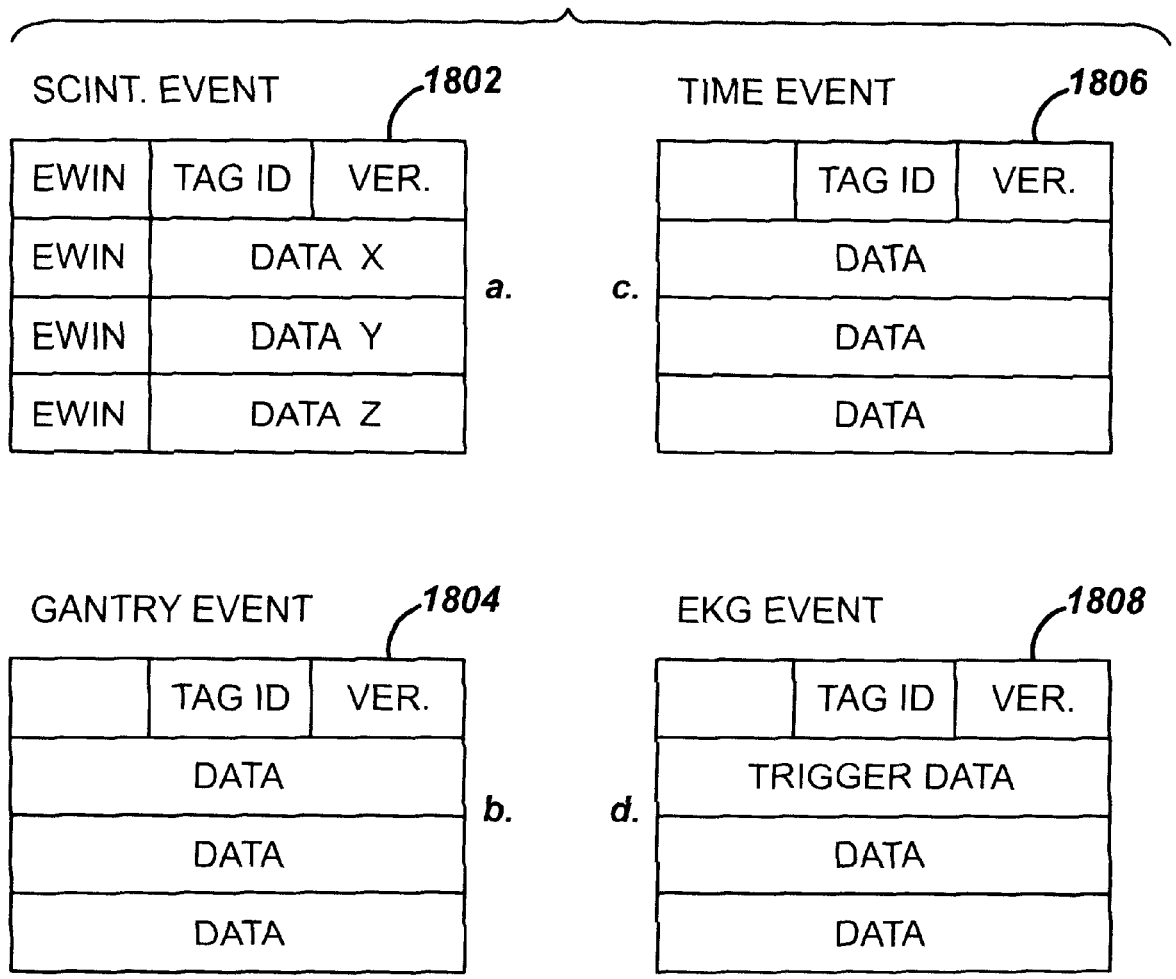
FIGS. 6a–6d illustrate the format of the data used in a constructed embodiment of the present invention.

Examples of the types of event data which may be provided by a detector are shown in FIG. 6. In this example each event word is 64 bits long. The words in this drawing are shown in four lines of sixteen bits each. FIG. 6a illustrates a scintillation event word 1802 with four energy window bytes EWIN of four bits each. The setting of one of these bits denotes one of sixteen energy windows in which the particular scintillation event was acquired. Typically a detector will only produce data for energy windows chosen by the camera operator. The TAG ID and TAG VERSION (VER.) bytes identify the data word as a scintillation event word. The TAG bytes provide information such as the detector number which produced the event. Data X and Data Y provide the x and y coordinate locations on the detector at which the event was sensed. The Data Z byte provides the energy number of the detected event.

FIG. 6b shows a format for a gantry event word 1804. Gantry event words provide information as to the current position of the gantry and hence the locations of the detectors. Gantry event data originates with sensors, controllers, and other devices associated with the gantry or from control programs for the gantry. The illustrated gantry event word 1804 has TAG ID and VER. bytes which identify the word as a gantry event word. The TAG bytes provide information as to the type of information contained in the gantry event word. The last three lines contain the data pertinent to the gantry event.

FIG. 6c gives an example of a time event word 1806. The acquisition system provides these words as time markers so that the other events of the camera can be oriented in time. Time events occur in regular intervals such as once every millisecond. The TAG bytes of the time event word denote the word as a time event word. The rest of the time event word comprises data giving the time information.

FIG. 6d illustrates an EKG event word 1808, which will be produced when a cardiac electrode unit 25 is used for a gated study. The TAG bytes identify the word as an EKG event word. A TRIGGER DATA byte provides information as to the trigger event, and the other data bytes of the EKG event word provide other information pertinent to the EKG event.

Other event words may also be present in the data stream provided by the detectors and entered into the ring buffer 1720. For example Start and Stop event words may be used to indicate the start of an image acquisition session and the conclusion of an image acquisition session.

Some examples will illustrate various studies which can be carried out simultaneously by an embodiment of the present invention. One example is imaging with two energy windows simultaneously. Consumer C1 is conditioned to look for scintillation event words in the ring buffer for which the EWIN#1 bit is set. Scintillation event data exhibiting this characteristic is selected and is binned to form pixels for a first image W1. Consumer C2 is conditioned to look for scintillation events in the ring buffer for which the EWIN#2 bit is set, and this scintillation event data is read by the Consumer C2 and binned to form pixels for a second image W2. A third Consumer C3 is conditioned to look for scintillation event words in which either bit EWIN#1 or bit EWIN#2 is set, and reads and bins this event data to produce pixels for a third image W1+W2. All three Consumers use gantry events and time events. A variation of this operation would be to use only a single Consumer to look for scintillation event words in which either bit EWIN#1 or bit EWIN#2 is set, and to thereafter sort and bin this event data into distinct images W1, W2, or W1+W2.

A second example of an application of the present invention is to perform gated and ungated studies simultaneously. Two Consumers C1 and C2 are separately conditioned for the two types of studies. In this example, Consumer C1 monitors the event data for EKG trigger event data, while Consumer C2 does not monitor this data. For example, C1 may be conditioned to acquire an image of data produced during a heart cycle interval occurring 600–700 milliseconds after the start of a heart cycle. The Consumer C1 would monitor the event data in the ring buffer until an EKG trigger event word is identified. Consumer C1 then begins reading scintillation event data and forwarding the event data to an image processor. When the count of time event words by C1 reaches the predefined time (600–700 milliseconds in this example), C1 stops binning the scintillation event words. Consumer C1 then monitors the event data for the next EKG event word, whereupon the process repeats for the next heart cycle.

While Consumer C1 is acquiring the gated heart data, Consumer C2 is acquiring ungated event data. For example, Consumer C2 may be conditioned to acquire scintillation event data continuously for 20 seconds, which covers many heart cycles. As Consumer C1 begins to monitor and acquire its gated acquisition data, the Consumer C2 acquires a continuous stream of event data for 20 seconds or 20 heart cycles, or some other selected period. Consumer C2 forwards the event data it selects to an image processor for binning of an ungated image.

This acquisition sequence, in which one Consumer acquires gated event data while another Consumer acquires ungated event data, is performed for each gantry position of the protocol. The simultaneous acquisitions are repeated for each gantry position based upon the detection of new gantry events by the Consumers. In a constructed embodiment the Consumers provide status of their acquisitions to a control program. When each Consumer has satisfied its needs for new event data at a particular gantry location, this status is reported to the control program. When all Consumers report that they are satisfied, the control program commands the movement of the gantry to the next detector position.

When acquisition data has been acquired from all of the gantry positions of the protocol, the study and its acquisition of the simultaneous images is complete. The clinician may find that the gated image is sufficient for a diagnosis and may make a diagnosis without examining the ungated image at all. Alternatively, the clinician may discover that the patient has experienced an irregular heartbeat during the study, and that this has caused the scintillation events to be inaccurately binned. The gated image may thus be nondiagnostic. The clinician can then examine the ungated image, which is not similarly affected by the irregular heartbeat. The ungated image may be sufficient for the clinician to conclude a diagnosis, which is thus made without conducting another study and without the need to redose the patient.

Other types of simultaneous studies are possible with an embodiment of the present invention. For instance, zoomed and unzoomed images may be produced simultaneously by conditioning the Consumers to select event data from the appropriate detector locations, and binning the event to the appropriate zoomed and unzoomed pixel resolution. As another example, both flow and wall motion images can be acquired simultaneously, as well as both perfusion and wall motion images.

One skilled in the art will appreciate that, since the simultaneous acquisitions are being made during the same sequence of gantry motion, the two studies must be those that can be performed during the extant gantry behavior. For example, a planar gated study (in which the detector head is stationary) and an ECT study (in which the detector head moves) cannot be performed simultaneously, since these two studies call for different detector motion. Accordingly, the control program which sets up the simultaneous protocols at the outset of the exam performs consistency checks of the multiple studies called for by the operator to assure that the two studies utilize the same gantry behavior.

What is claimed is:

1. A nuclear camera system comprising:
    a source of event data exhibiting a given gantry behavior;
    a first data path, responsive to the event data, which acquires event data satisfying at least a first characteristic;
    a second data path, responsive to the event data, which acquires event data satisfying at least a second characteristic; and
    an image processor, responsive to the first and second data paths, which produces image data sets exhibiting the first and second characteristics.

2. The nuclear camera system of claim 1, further comprising a scintillation detector, and a gantry which moves a scintillation detector,
    wherein the source of event data is the detector.

3. The nuclear camera system of claim 2, further comprising:
    a ring buffer having an input coupled to the source of event data and an output coupled to the first and second data paths.

4. The nuclear camera system of claim 2, wherein the first characteristic comprises gated acquisition data and the second characteristic comprises ungated acquisition data.

5. The nuclear camera system of claim 2, wherein the first characteristic comprises a first energy window and the second characteristic comprises a second energy window.

6. The nuclear camera system of claim 2, wherein the first characteristic comprises a first zoom characteristic, and wherein the second characteristic comprises a second zoom characteristic.

7. The nuclear camera system of claim 1, wherein the source of event data is a nuclear camera data storage device.

8. The nuclear camera system of claim 1, wherein the image processor comprises:
    means for binning event data from the first data path; and
    means for binning event data from the second data path.

9. The nuclear camera system of claim 8, wherein the means for binning event data from the first data path produces a histogram of event data satisfying a first characteristic; and
    wherein the means for binning event data from the second data path produces a histogram of event data satisfying a second characteristic.

10. The nuclear camera system of claim 1, further comprising:
    means for enabling a user to produce a protocol for acquiring two data sets during the same procedure; and
    wherein the means for enabling comprises means for checking that acquisition of the two data sets is consistent with the given gantry behavior.

11. The nuclear camera system of claim 1, wherein the first data path comprises a first consumer conditioned to identify event data which is consistent with the first characteristic; and
    wherein the second data path comprises a second consumer conditioned to identify event data which is consistent with the second characteristic.

12. The nuclear camera system of claim 1, wherein the event data comprises at least three of: scintillation event data words, gantry event data words, time event data words, and EKG event data words.

13. A nuclear camera system comprising:
    a source of event data exhibiting a given gantry behavior;
    a first processor, responsive to the source of event data, which acts to identify event data associated with gated data acquisition;
    a second processor, responsive to the source of event data, which acts to identify event data associated with ungated data acquisition;
    a first image processor, responsive to event data identified by the first processor, which acts to create a gated event histogram; and
    a second image processor, responsive to event data identified by the second processor, which acts to create an ungated event histogram.

14. The nuclear camera system of claim 13, wherein the event data comprises: scintillation event data words, gantry event data words, time event data words, and EKG event data words.

15. A nuclear camera system comprising:

a source of scintillation camera event data exhibiting a given gantry behavior;

an event data selector, responsive to the source of event data, which acts to identify a first sequence of event data associated with a first acquisition type, and a second sequence of event data associated with a second acquisition type; and an image processor, responsive to the identified sequences, which acts to produce different images which utilize the first and second sequences.

16. The nuclear camera system of claim 15, wherein the event data produced by the source of event data is produced during a single imaging procedure, wherein the different images are produced utilizing event data produced during the single imaging procedure.

* * * * *